US005247842A

United States Patent [19]

[11] Patent Number: 5,247,842

Kaufman et al.

[45] Date of Patent: Sep. 28, 1993

[54] ELECTROSPRAY APPARATUS FOR PRODUCING UNIFORM SUBMICROMETER DROPLETS

[75] Inventors: Stanley L. Kaufman, New Brighton; Fahimeh Zarrin, St. Paul; Frank Dorman, Minneapolis, all of Minn.

[73] Assignee: TSI Incorporated, St. Paul, Minn.

[21] Appl. No.: 767,670

[22] Filed: Sep. 30, 1991

[51] Int. Cl.[5] .............................................. G01N 1/28

[52] U.S. Cl. ...................................... 73/865.5; 356/37

[58] Field of Search ................. 73/865.5, 61.72, 64.56; 324/71.4; 356/36, 37, 326–330, 335, 336, 441, 442; 250/372, 373, 311, 472.1, 288 R, 288 A; 422/82.05–82.11; 436/36, 18; 239/690, 690.1, 692, 71

[56] References Cited

U.S. PATENT DOCUMENTS

| | | | |
|---|---|---|---|
| 3,169,524 | 2/1965 | Langevin . | |
| 3,462,609 | 8/1969 | Beattie | 356/37 |
| 3,589,606 | 12/1968 | Fish . | |
| 3,669,542 | 6/1972 | Capellaro | 356/36 |
| 3,953,792 | 4/1976 | Fletcher et al. | 324/71.4 |
| 4,049,200 | 9/1977 | Sobol . | |
| 4,284,496 | 8/1981 | Newton | 324/71.4 |
| 4,301,970 | 11/1981 | Craighero . | |
| 4,501,965 | 2/1985 | Douglas | 250/288 |
| 4,531,056 | 7/1985 | Labowsky et al. | 250/288 A |
| 4,635,857 | 1/1987 | Hughes . | |
| 4,640,140 | 2/1987 | Burghoffer et al. | 73/863.22 |
| 4,790,650 | 12/1988 | Keady | 356/37 |
| 4,794,086 | 12/1988 | Kasper et al. | 73/61.71 |
| 4,861,988 | 8/1989 | Henion et al. | 250/288 A |
| 5,015,845 | 5/1991 | Allen et al. | 250/288 A |

FOREIGN PATENT DOCUMENTS

| | | | |
|---|---|---|---|
| 1463953 | 12/1966 | France | 73/865.5 |

OTHER PUBLICATIONS

"Method for the Electrospray Ionization of Highly Conductive Aqueous Solutions", Chowdhury et al, *Anal. Chem.*, 1991, vol. 63, No. 15, Aug. 1, 1991, pp. 1660–1664.

*IEEE Transactions on Industry Applications*, "The Electrohydrodynamic Atomization of Liquids", pp. 527–535, vol. IA>, No. 3, May/Jun. 1986, Smith.

Ultramicroscopy 16 (1985) 1–8, *North-Holland Physics Publishing Division*, "In Situ High Voltage Tem Observation of an Electrohydrodynamic (EHD) Ion Source", Benassayag et al, pp. 1–8.

*Journal of Research of the National Institute of Standards and Technology*, vol. 96, No. 2, Mar.–Apr. 1991, Kinney et al, "Use of the Electrostatic Classification Method to Size 0.1 mm SRM Particles—A Feasibility Study", pp. 14714 176.

*The FASEB Journal*, vol. 4, Oct. 1990, pp. 3144–3151, Edstrom et al, "Viewing Molecules with Scanning Tunneling Microscopy and Atomic Force Microscopy".

*Science*, vol. 246, Oct. 6, 1989, pp. 64–70, Fenn et al, "Electrospray Ionization for Mass Spectrometry of Large Biomolecules".

*Analytical Chemistry*, vol. 62, No. 9, May 1, 1990, Smith et al, "New Developments in Biochemical Mass Spectrometry: Electrospray Ionization", pp. 882–899.

(List continued on next page.)

*Primary Examiner*—Robert Raevis
*Attorney, Agent, or Firm*—Haugen and Nikolai

[57] ABSTRACT

An electrospray nebulizer generates an aerosol comprised of submicrometer droplets substantially uniform in size. A liquid sample is supplied at a controlled rate to a capillary needle of the nebulizer, and droplets are formed due to an electrical field in the region about the needle discharge. The tendency of the droplets to disintegrate due to Coulomb forces is counteracted by sources of ionizing radiation within the nebulizer. The ions reduce the charge in each droplet while solvent evaporation reduces the diameter of the droplet. To further ensure against Coulomb disintegration, a controlled air sheath is introduced to the nebulizer for transporting droplets more rapidly downstream. Optionally, solvent vapor can be introduced into the air flow to reduce the rate of solvent evaporation within the nebulizer, and ions can be added to the air flow upstream of the needle discharge.

41 Claims, 5 Drawing Sheets

OTHER PUBLICATIONS

*J. Aerosol Science*, vol. 21, Suppl. 1, pp. 5673–5676, 1990, De La Mora et al, "Generation of Submicron Monodisperse Aerosols in Electrosprays".

*J. Aerosol Science*, vol. 21, Suppl. 1, pp. 5669–5672, 1990, Meesters et al, "A Monodisperse-Aerosol-Generator, Using the Taylor Cone, for the Production of IMM Droplets".

Abstracts for Patent Nos. 4,999,943; 4,977,320; 4,935,624; 4,885,076; 4,842,701; 4,748,043; 4,542,293; 4,531,056; 4,209,696.

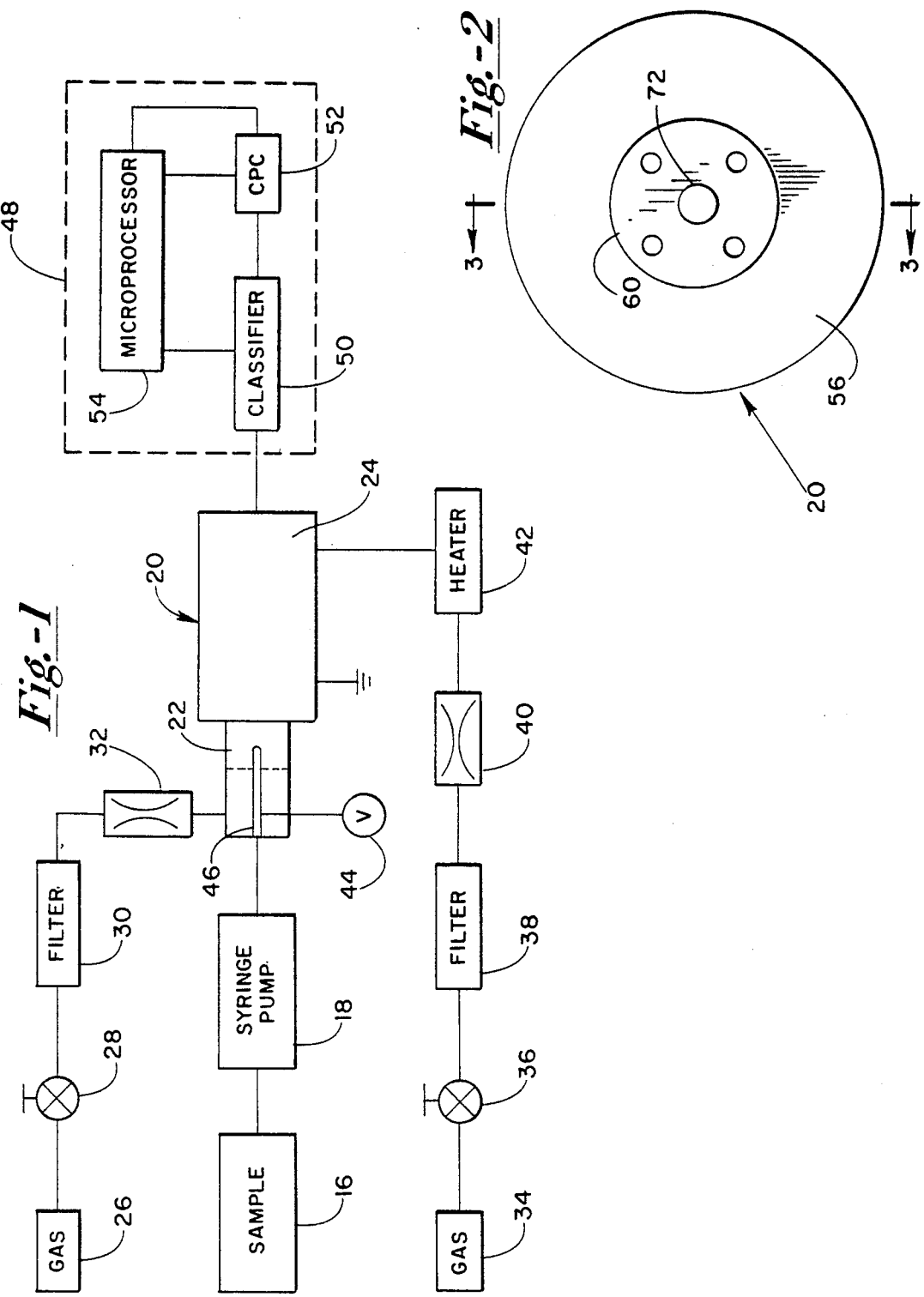

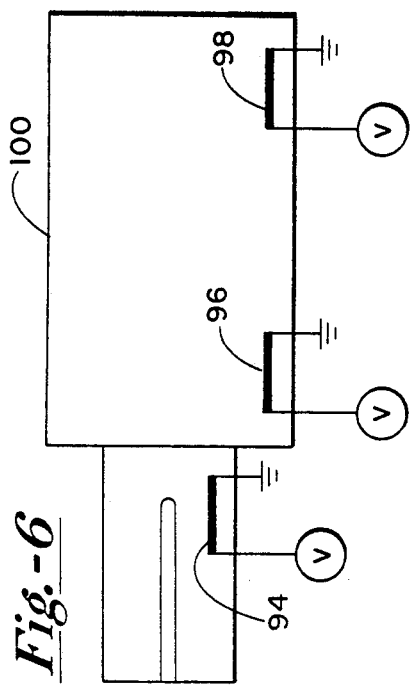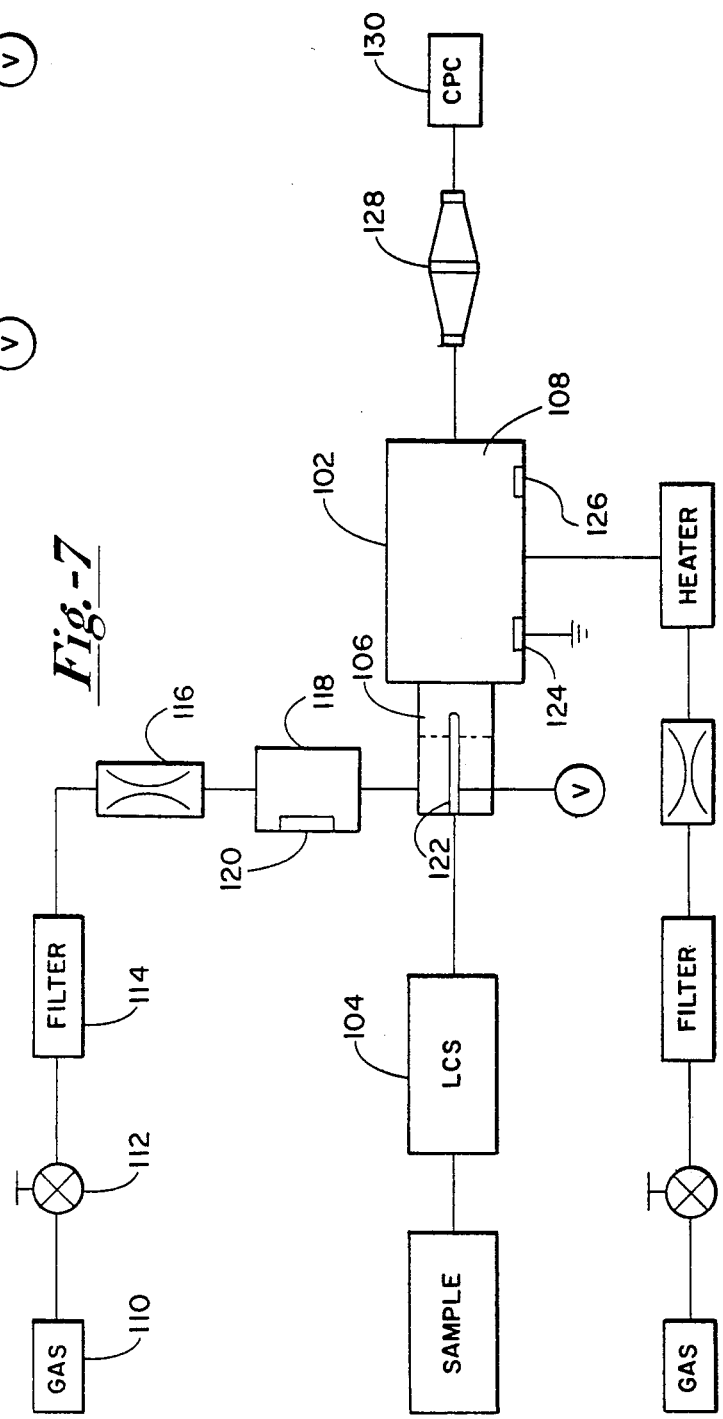

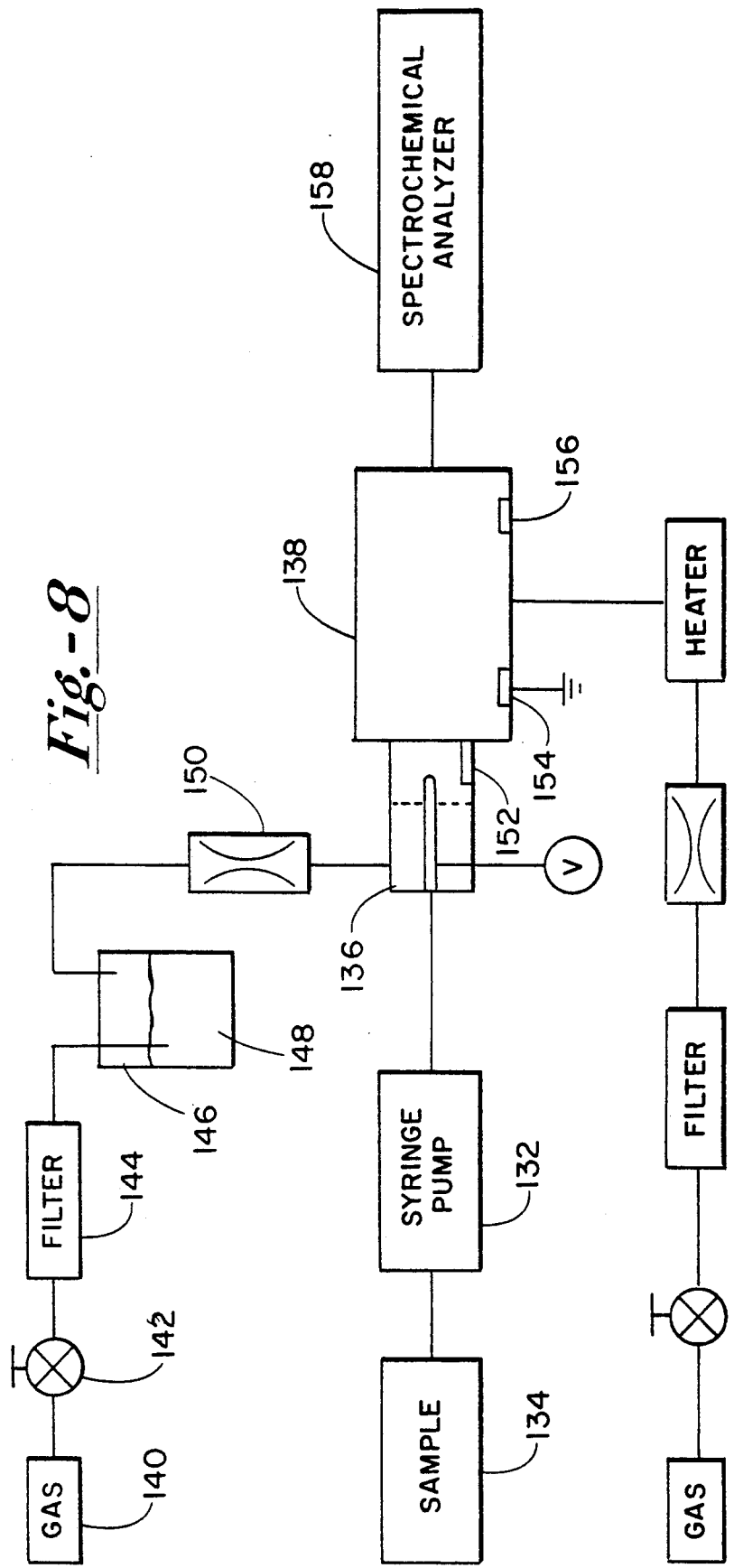

ELECTROSPRAY APPARATUS FOR PRODUCING UNIFORM SUBMICROMETER DROPLETS

BACKGROUND OF THE INVENTION

The present invention relates to analytical devices for detecting and characterizing minute particles and macromolecules suspended or dissolved in liquid samples, and more particularly to a means for generating droplets of the liquid samples, of a size and uniformity to enhance the effectiveness of such analytical devices.

The ability to analyze liquid solutions is becoming increasingly important in a wide variety of fields including medicine, pharmaceuticals, production of polymers, paints and dyes, environmental science and genetics. A variety of techniques including atomic absorption spectrometry, atomic emission spectrometry, inductive coupled plasma, light scattering, and mass spectrometry, are used to detect, characterize and determine concentrations of solutes, suspensions and residue in liquid solutions. In connection with these techniques, it is highly preferred to convert the liquid sample into aerosol form, typically by using a nebulizer.

While various types of nebulizers are known, including ultrasonic, pneumatic, frit and thermospray, an electrospray nebulizer is preferred in many applications due to its ability to generate small and uniform droplets, and in its relatively high efficiency, in terms of sample droplets delivered to a detector as compared to the sample uptake rate.

In the electrospray nebulizer, electrically conductive liquid is supplied at a controlled rate to a capillary tube. A voltage differential between the capillary tube and a surrounding chamber wall creates an electrostatic field that induces a surface charge in liquid emerging from the tube. Electrostatic or "Coulomb" forces disperse the liquid into a fine spray of charged droplets. To produce the spray, each droplet is charged near the Rayleigh limit (at which point electrostatic repulsion overcomes surface tension).

When analyzing macromolecules, colloids or other small particles of interest, the particles are dispersed in a liquid, the liquid is sprayed in small droplets, then the droplets are dried, leaving the particles in aerosol form. An exemplary use of an electrospray nebulizer is disclosed in U.S. patent application Ser. No. 07/564,004, filed Jun. 28, 1990 and assigned to the assignee of this application. An apparatus for measuring concentrations of macromolecules and colloids in a liquid sample, uses an electrospray atomizer to receive a liquid analyte, after separation by a liquid chromatography system. Within the atomizer, an electrical field charges the liquid emerging at the tip of a needle, whereby the liquid is dispersed into a fine spray of charged droplets. As solvent evaporates from each droplet, charge density on the droplet surface increases until the Rayleigh limit is reached. The resulting instability causes the droplet to disintegrate into smaller droplets. The aerosol output of the electrospray atomizer is provided to a condensation nucleus counter, either directly or through diffusion screens that filter smaller particle sizes.

Even "pure" liquids contain some non-volatile material. Accordingly, each droplet contains a proportion of a residue, and further may contain one of the particles under study. The particle concentration in the liquid sample, and the volume of the droplets as initially formed, are kept to a minimum to avoid production of "clusters" (droplets containing two or more of the particles under study).

The size of residue particles depends upon residue concentration and initial droplet size. For example, a one part per million impurity level results in a residue particle of about one percent of the diameter of the original droplet (assuming the dried material and the liquid have approximately the same density). Thus, a nebulizer producing droplets 10 micrometers in diameter would produce residue particles having a diameter of about 100 nanometers.

Such residue particles are inconsequential, so long as particles under study are relatively large. However, residue particles cause substantial interference or artifacts that interfere with detecting and characterizing smaller particles. In many of the abovementioned fields, there is a strong interest in studying particles as small as three nanometers in diameter, e.g. macromolecules and colloids such as synthetic polymers, proteins, viruses and particles of concern in connection with maintaining semiconductor production facilities. To reduce residue artifacts, it is necessary either to reduce the non-volatile impurity concentration, or to generate smaller droplets.

Given the difficulty in producing and handling ultra pure liquids, generating smaller droplets appears to be the logical solution. However, the Coulomb forces employed to generate droplets also cause droplet disintegration shortly after formation. More particularly, as liquid evaporates from the droplets, surface charge density on the droplets increases until the Rayleigh limit is reached, at which point the Coulomb repulsive force becomes the same order as cohesive forces such as surface tension. The resulting instability causes the original droplet, sometimes referred to as the parent or primary droplet, to disintegrate into smaller droplets. The primary droplet appears to eject several small droplets, removing a substantial proportion of the total charge. The parent droplets and fragments continue to evaporate and can experience further fragmentations. The resulting distribution of droplet sizes is broad, i.e. non-uniform.

Therefore, it is an object of the present invention to provide a device for generating uniform droplets having diameters of less than one micrometer.

Another object of the invention is to provide a system for detecting macromolecules, colloids and other particles of interest having diameters in the range of 3–1,000 nanometers, substantially without interference from residue artifacts.

A further object is to provide a source of uniform aerosols for testing particle detection and classification devices within precisely defined ranges of particle diameters.

Yet another object is to provide a means for preparing uniform droplets sufficiently small to isolate single individual biological molecules, e.g. nucleic acids, proteins, and carbohydrates, for subsequent observation.

SUMMARY OF THE INVENTION

To achieve these and other objects, there is provided an apparatus for generating aerosols, based on liquid samples. The apparatus includes an electrospray means having an electrospray inlet and an electrospray discharge. The electrospray means receives the liquid sample at the electrospray inlet and generates multiple substantially uniformly sized electrically charges droplets of the liquid sample at the discharge. A means is provided for supplying the liquid sample to the electrospray means. An evaporation means defines a droplet evaporation region proximate the electrospray discharge and extending downstream of the electrospray discharge, for reducing the size of the droplets by evaporation as the droplets progress downstream through the evaporation region, to form an aerosol.

A charge neutralizing means is disposed proximate the electrospray discharge and along the evaporation region. The neutralizing means reduces the electrical charge of each droplet of the liquid sample as the droplet exits the electrospray means. The neutralizing means further continues to reduce the electrical charge of each droplet as it progresses through the evaporation region, to prevent the droplets from disintegrating due to repulsive Coulombic forces.

The preferred neutralizing means is a source of ionizing radiation, for example radioactive polonium emitting alpha particles or a photon ionization source, or another source of ions, such as a corona discharge. The source of ions is positioned proximate the electrospray discharge, such that the droplets encounter the ions virtually immediately upon their formation. Additional sources of ions can be positioned further downstream along the evaporation region, so that the droplets are further neutralized as they proceed downstream.

The evaporating means advantageously includes an enclosure defining an evaporation chamber having an entrance orifice just downstream of the electrospray discharge. The enclosure further can define an electrospray chamber adjacent and upstream of the evaporation chamber, with the electrospray discharge within the electrospray chamber. An electrically conductive plate or wall separates the evaporation chamber from the electrospray chamber and is electrically biased to attract the newly formed charged droplets toward the evaporation chamber. The entrance orifice, disposed in the wall, admits the droplets into the evaporation chamber.

Preferably a gas is supplied to the electrospray chamber, and flows in a sheath or stream through the entrance orifice into the evaporation chamber, to carry the charged droplets into the evaporation chamber. A flow guide plate inside the electrospray chamber tends to diminish any turbulence in the gas flow, whereby newly formed droplets are carried smoothly and efficiently from the electrospray discharge into the evaporation chamber.

The nebulizer is further enhanced by the addition of a vapor to the gas sheath, e.g. by adding the vapor to the gas supplied to the electrospray chamber. The vapor tends to retard evaporation of the droplets, further reducing the chance for droplet disintegration. The vapor can be water vapor, or more preferably, vapor of the solvent in the liquid sample. To further reduce evaporation rates, the air or other gas can be supplied to the evaporation chamber at a moderate temperature, i.e. with no preheating.

Thus, according to the present invention, electrostatically generated droplets of a liquid sample are uniform in size (i.e. monodisperse), not only as they are formed at the electrospray discharge, but also as they progress through the evaporation region to the nebulizer exit. The droplets proceed downstream across the evaporation region while subject to uniform conditions that substantially prevent their disintegration under Coulombic forces. Rayleigh disintegration is prevented, first by controlling the level of electrical charge in the droplets, more particularly in subjecting the droplets to charge-neutralizing radiation substantially immediately upon their formation and continuously as they progress along the evaporation region. The droplet carrying gas sheath provides further control, in more rapidly transferring droplets downstream to neutralizing radiation, effectively diminishing the rate of evaporation per unit distance of downstream travel. A further control is the amount of vapor in the gas stream, which of course further reduces droplet evaporation.

The control of conditions in the nebulizer, whereby droplet disintegration is prevented, has yielded a surprising degree of size uniformity among droplets and other aerosols discharged by the nebulizer. This feature substantially enhances the utility and effectiveness of the nebulizer, particularly in combination with known devices for detecting and characterizing extremely small particles. For example, the nebulizer of the present invention can provide its output to a condensation particle counter (such as described in U.S. Pat. No. 4,790,650) to monitor residue, measure concentrations of compounds and detect compounds in the threshold size range of the condensation particle counter (i.e. 3–1,000 nm diameter). The improved nebulizer can be used as a source of particles of a narrow, precisely controlled size range, to test a filter or characterize a particle measuring instrument. Further, the nebulizer can be used to deposit small and uniform droplets, to isolate single molecules (e.g. viruses, nucleic acids, proteins and carbohydrates) for analysis by techniques such as atomic force microscopy or electron microscopy.

Generally, the ability to control the nebulizer and avoid Coulomb disintegration, enables electrostatic generation of primary droplets smaller in size than previously believed feasible. More particularly, primary droplets are formed with diameters in the range of from about 140 to 860 nanometers in diameter, for residue particle diameters of substantially less than 10 nanometers, assuming a particle diameter of about 1 percent of the primary droplet diameter. Accordingly, macromolecules, colloids and other particles of interest with diameters in the range of 10 nanometers can be detected and characterized successfully using presently available analytical apparatus, such as the abovementioned condensation particle counter.

IN THE DRAWINGS

For a further appreciation of the above and other features and advantages, reference is made to the following detailed description and to the drawings, in which:

FIG. 1 is a schematic view of a system for detecting and characterizing small particles in accordance with the present invention;

FIG. 2 is a forward elevational view of an electrospray nebulizer employed in the system of FIG. 1;

FIG. 6 is a schematic view of an alternative electrospray nebulizer;

FIG. 7 is a schematic view of a particle separation and detection system according to another embodiment of the invention;

FIG. 8 is a schematic view of a spectrochemical particle analyzing system according to a further embodiment of the invention.

DETAILED DESCRIPTION OF THE PREFERRED EMBODIMENTS

Figure 3:
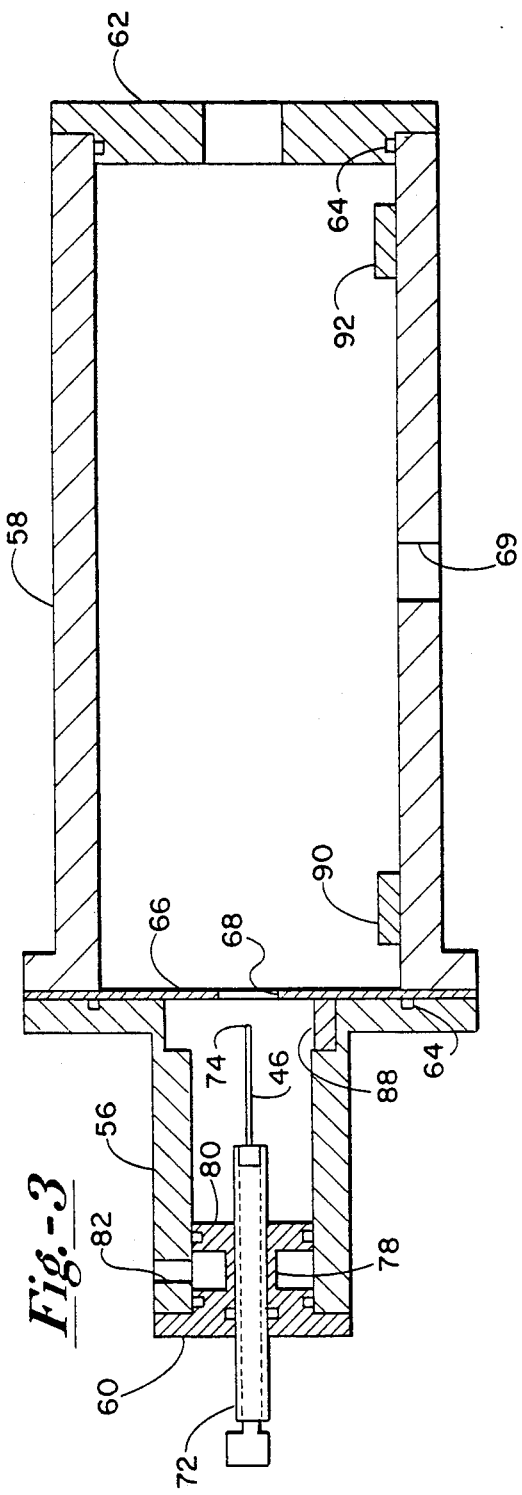
FIG. 3 is a sectional view taken along the line 3—3 in FIG. 2.

Turning now to the drawings, there is shown in FIG. 1 a system for detecting and characterizing particles in the range of from 3 to 1,000 nanometers in diameter. Initially, the particles of interest are part of a liquid sample or solution held in a container 16. A syringe pump 18, loaded with the liquid from the container, supplies the liquid to an electrospray nebulizer 20 at a steady, controlled rate, e.g. about 0.6 microliters per minute. The liquid of the sample can be water, with a volatile additive, e.g. either nitric acid or hydrochloric acid, added in a predetermined amount to control the electrical conductivity of the solution. Typically, the pH of the liquid sample is between four and five. Other additives are suitable for increasing conductivity, e.g. acetic acid and ammonium acetate. The primary reason for enhancing conductivity is to enable nebulizer 20 to produce smaller droplets, and thus smaller particles.

The nebulizer includes two chambers, an electrospray chamber 22 and an evaporation chamber 24. Syringe pump 18 supplies the liquid to the electrospray chamber. Another input to electrospray chamber 22 is a steady rate supply of a filtered gas, typically air. More particularly, air under pressure in a container 26 is provided through a valve 28 to a filter 30, and then via controlling orifice 32 to the nebulizer. Filter 30 is a high efficiency pleated glass filter available from TSI Incorporated of St. Paul, Minn. and designated as Model 3074. Optionally, a heater (not illustrated) can be interposed between critical orifice 32 and nebulizer 20. Preferably, however, heated air (or another gas) is supplied to the nebulizer at evaporation chamber 24. As illustrated, air from a supply 34 is directed through a valve 36, a filter 38 and a controlling orifice 40 to a heater 42. Air from the heater enters the evaporation chamber, to maintain the temperature within chamber 24 at 32 degrees C. or more, to promote evaporation of droplets of the liquid sample.

A high voltage source 44 is electrically connected to a capillary needle 46 of the nebulizer while portions of the nebulizer electrically isolated from the needle are connected to ground. Under certain circumstances it is preferable to ground the needle and bias such electrically isolated portions. In any event, the key is to create a high potential difference between the needle and the isolated portions.

The output of electrospray nebulizer 20 is provided to a differential mobility particle sizer (DMPS) 48, which consists of an electrostatic classifier 50 and a condensation particle counter (CPC) 52. An appropriate DMPS is available from TSI Incorporated as TSI Model 390074 including a TSI Model 3071 electrostatic classifier and a TSI Model 3025 condensation particle counter (sometimes known as a condensation nucleus counter).

The output of electrospray nebulizer 20 is an aerosol, and can include droplets (substantially reduced in size but not yet fully evaporated), non-volatile residue from droplets that contained dissolved impurities, and isolated particles under study (e.g. macromolecules or colloids) together with non-volatile residue. The particle concentration in the liquid sample is sufficiently low, and the size of generated droplets is kept sufficiently small, thus substantially reducing the probability of generating doublets or other clusters of two or more molecules or colloids within a single droplet. For further information on this principle, reference is made to the aforementioned application Ser. No. 07/564,004.

The electrospray nebulizer output is provided to classifier 50, which operates based on the monotonic relationship between electrical mobility and size, of singly charged particles. Particles received in classifier 50 are introduced into a bipolar charger where they collide with bipolar ions, reaching an equilibrium state of known proportions of neutral particles, singly charged particles, and particles having multiple charges. Then particles are directed to a differential mobility analyzer having two concentric metal cylinders. The particles and air flow downwardly from the top of a gap between the cylinders, with a D.C. voltage applied to the inner cylinder while the outer cylinder is grounded. Particles of the appropriate polarity are attracted to the inner cylinder. Particles of a predetermined size reach the region of a narrow opening, where they are swept through by an air stream. Smaller particles adhere to the inner cylinder above the opening, while larger particles continue to descend below the opening.

Particles leaving electrostatic classifier 50 are detected and counted in condensation particle counter 52. In the condensation particle counter, the particles proceed through a region saturated with a vapor, e.g. n-butyl alcohol. Then, the particle stream is cooled sufficiently to supersaturate the vapor, whereupon the vapor condenses onto the particles, forming aerosol droplets much larger in diameter than the particles entering the CPC. Downstream of the condenser, the aerosol droplets are detected by an optical detector including a laser and associated optics. For further information about the CPC, reference is made to U.S. Pat. No. 4,790,650 (Keady), assigned to the assignee of this application.

The output of the CPC is an electrical signal responsive to particles that pass through a viewing volume defined by the laser and optics. The signal is provided to a microcomputer 54, which analyzes the data and controls the classifier and the CPC. A suitable microcomputer is available from International Business Machines Corporation, as the IBM XT Model 286 personal computer.

A salient feature of the present invention is the manner in which electrospray nebulizer 20 enhances the performance of DMPS 48, in particular by providing an aerosol composed of uniformly sized droplets or particles. The high degree of uniformity primarily is the result of the nebulizer structure as illustrated in FIGS. 2–5, although stabilized inputs to the nebulizer can enhance uniformity.

Various sections of the nebulizer are secured to one another to provide a fluid-tight enclosure. These sections include an electrospray cylinder 56, an evaporation cylinder 58, a capillary mounting end section 60, and an exit end section 62 opposite the capillary mounting section. All of the sections preferably are constructed of brass, stainless steel or other metal, and are provided with rectangular grooves, e.g. as indicated at 64, to accommodate sealing rings. A circular plate 66, also of brass or stainless steel, is mounted between the electrospray and evaporation cylinders to provide an electrically conductive wall between electrospray chamber 22 and evaporation chamber 24. An orifice 68 having a diameter of approximately 0.18 inches is located at the center of plate 66. An opening 69 through evaporation cylinder 58 admits heated and filtered air to the evaporation chamber. Further openings can be provided, if desired.

End section 60, when secured to electrospray cylinder 56 by screws, supports capillary needle 46 in a concentric alignment with the electrospray chamber. More particularly, the capillary needle is mounted within an elongate cylindrical metal casing 70, surrounded by an insulative jacket 72 constructed of a material selected for toughness, e.g. Delrin brand acetal (a plastic) available from duPont. The capillary needle, casing and jacket are housed within end section 60, with the jacket electrically isolating the capillary needle from the aluminum enclosure. Capillary needle 46 is elongate and suited for forming small droplets, with an outside diameter of about 0.02 inches and an interior (lumen) diameter of about 50 micrometers. A discharge 74 of the needle is positioned approximately 0.22 inches upstream of plate 66, concentric with orifice 68.

Figure 5:
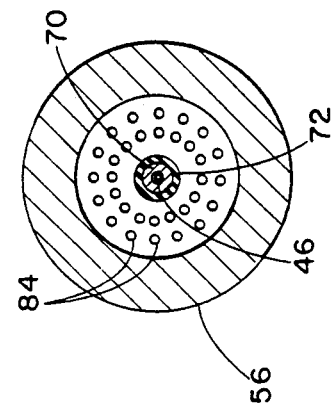
FIG. 5 is a sectional view taken along the line 5—5 in FIG. 4.
Figure 4:
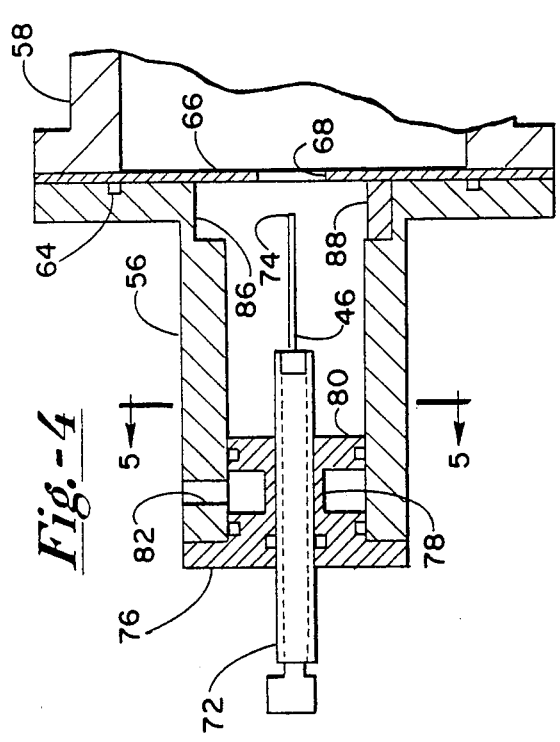
FIG. 4 is an enlarged view of a portion of FIG. 3.

End section 60 has three segments, including an end cap 76, a narrow shank 78, and a flow guide plate 80. The shank is aligned with an opening 82 through electrospray cylinder 56, through which the filtered air enters the electrospray chamber. As seen in FIG. 5, multiple 0.04 inch diameter guide apertures 84 are formed through guide plate 80 in a pattern of circles concentric on capillary needle 46. Guide apertures 84 cooperate to channel the flow of air, to form an air "sheath" surrounding capillary needle 46 and flowing along the needle and into evaporation chamber 24 through orifice 68. Guide apertures 84 substantially reduce turbulence in the gas flow, permitting an increased flow velocity whereby the gas sheath more rapidly transfers charged droplets into the evaporation chamber.

Electrospray chamber 22 includes a radially enlarged region 86 near plate 66. Along this region, a strip 88 of source of ionizing radiation within the electrospray chamber, particularly along the region between discharge 74 and orifice 68. Similar strips are mounted to the evaporation cylinder as indicated at 90 and 92, and provide ionizing radiation throughout the evaporation chamber. The ions encounter the sample droplets produced at discharge 74, and reduce their electrical charge, tending to neutralize the droplets. Due to the presence of strip 88, droplets encounter the ions virtually immediately upon their formation, which minimizes the potential for droplet disintegration due to Coulombic forces.

Strips 90 and 92 provide ionizing radiation in the evaporation chamber, to prevent Coulomb disintegration as droplets of the sample proceed through the evaporation chamber and for the further purpose of preventing the droplets from clinging to the evaporation cylinder.

It has been found that mounting radiation sources to the evaporation cylinder alone provides sufficient neutralization, if a source of the radiation is positioned sufficiently upstream to provide substantial radiation at orifice 68. Also, it is to be recognized that ion sources other than polonium strips can be employed, for example corona discharge sources 94, 96 and 98 as indicated in a nebulizer 100 (FIG. 6), a photon ionization source, or any radioactive material emitting alpha particles or beta particles.

When electrospray nebulizer 20 is to be used, voltage source 44 is connected to bias capillary needle 46 to a predetermined voltage in the range of from about 1.5-10 kilovolts, or more preferably 2-3 kilovolts. Syringe pump 18 supplies that sample solution at a steady rate of about 0.6 microliters per minute. Filtered air is supplied to the electrospray chamber 22 at the rate of about 2.5 liters per minute. The applied voltage creates an electrical field between capillary needle 46 and the surrounding grounded structure, in particular between discharge 74 and plate 66. As the sample solution emerges at the discharge, the surface of the liquid is charged, with Coulombic forces eventually overcoming cohesive forces such as surface tension, thereby causing a primary droplet to break away from the liquid remaining in the needle. Multiple repetitions of this phenomenon create a mist of solution droplets, substantially uniform in their diameter. The primary droplets are attracted toward plate 66 due to their charge, and carried through orifice 68 in the air sheath.

Almost immediately as they emerge from capillary needle 46, the solution droplets begin to shrink due to evaporation of the volatile solvent of the sample solution. If each of the droplets were to retain its electrical charge, the surface charge density would of course increase as the droplet size is reduced. Eventually, Coulombic forces would overcome cohesive forces such as surface tension, causing each droplet to disintegrate into a plurality of smaller droplets. Coulomb disintegration, occurring generally throughout the aerosol, would destroy the size uniformity of the droplets.

The polonium strips and guide plate 80 are features utilized to control conditions within the nebulizer, thus to prevent Coulomb disintegration. More particularly, ions produced by the alpha particle radiation reduce the charge of each droplet as it is reduced in size, retarding what otherwise would be a rapid increase in charge density at the surface of each droplet. The guide plate channels and controls the air flow, permitting a higher velocity air sheath. Consequently, droplets are transmitted more rapidly to the evaporation region, effectively reducing the rate of evaporation per unit length of aerosol travel. As the consequence of these features, the charged droplets remain uniform in size, not only within electrospray chamber 22 but throughout their travel across evaporation chamber 24, so that a monodisperse aerosol is presented to the differential mobility particle sizer or other instrument. In fact, it is the particle size uniformity of the nebulizer output that allows use of the DMPS in lieu of the chromatography system and CPC described in the aforementioned application Ser. No. 07/564,004, for a faster, less cumbersome system that affords improved resolution.

FIG. 7 illustrates an electrospray nebulizer 102 in a system involving particle separation based on liquid chromatography. The output of a liquid chromatography system 104, i.e. a separated liquid sample solution, is provided at a controlled rate to electrospray nebulizer 102 which is substantially identical to nebulizer 20 and has a electrospray chamber 106 and an evaporation chamber 108. An air supply 110, a valve 112, a filter 114 and a controlling orifice 116 are employed in providing filtered air to the electrospray chamber. In accordance with a further aspect of the present invention, air from the critical orifice travels through a chamber 118 on its way to the nebulizer. A polonium strip 120, or other suitable source of ionizing radiation mounted within chamber 118, produces bipolar ions within the chamber.

These ions are swept along in the air stream and sheath surrounding a capillary needle 122 of the nebulizer, thus to prevent fragmentation of the droplets at the earliest possible stage. This prevents the loss of droplets to the walls of electrospray chamber 106. Further polonium strips 124 and 126 are positioned within evaporation chamber 108. In view of polonium strip 120, a similar strip within the electrospray chamber is not necessary, although a strip could be utilized in chamber 106, if desired. The nebulizer output is provided to a diffusion screen 128, then to a condensation particle counter 130.

FIG. 8 illustrates a further embodiment system in which particles are subject to spectrochemical analysis. More particularly, a syringe pump 132 meters a liquid sample solution, loaded from a container 134, into an electrospray chamber 136 of an electrospray nebulizer 138. As before, air from a supply 140 is directed through a valve 142 to a filter 144. From filter 144, however, the air is provided to a closed container 146 containing a liquid 148. Air exiting the container thus includes a vapor of the liquid. The vapor-containing air proceeds through a controlling orifice 150, and into electrospray chamber 136. Ionization radiation sources 152, 154 and 156 in the nebulizer prevent Coulomb fragmentation, in the manner previously described.

The output of electrospray nebulizer 138 is provided to a spectrochemical configuration 158, which can include instruments for known spectrochemical techniques such as inductive coupled plasma, atomic absorption spectrometry, and atomic emission spectrometry.

Figure 9:
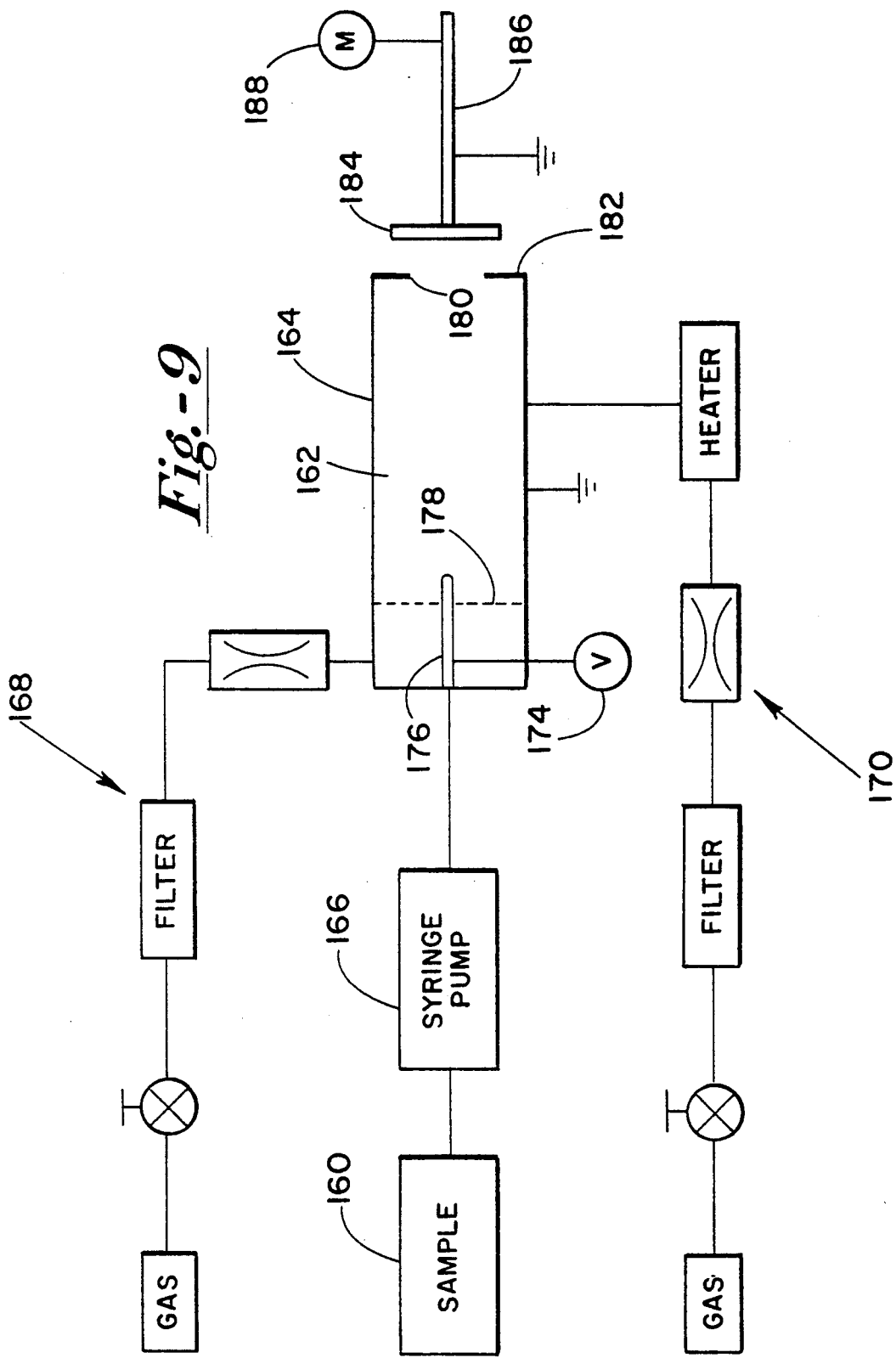
FIG. 9 is a schematic view of biomedical particle analysis system according to yet another embodiment of the invention.

FIG. 9 illustrates a system for studying individual biological molecules, e.g. nucleic acids, proteins, carbohydrates and viruses. The molecules of interest are dispersed in a liquid medium such as water, alcohol or a buffer. The solution, consisting essentially of the medium and molecule dispersion from a container 160, is supplied at a steady rate to a chamber 162 of an electrospray nebulizer 164 using a syringe pump 166. For example, molecules of the enzyme phosphorylase kinase can be prepared in a 0.1 millimolar tris buffer having a specific conductivity of 64 micromhos/cm and a pH of 7 for this purpose. Filtered air also is supplied to the electrospray chamber as indicated generally at 168, and a supply of heated and filtered air is provided to the nebulizer, as seen at 170. A high voltage source 174 biases a capillary needle 176 to a predetermined level, while surrounding structure is grounded.

Electrospray nebulizer 164 differs from previously described nebulizers in that it defines a single chamber rather than separate electrospray and evaporation chambers. A flow guide plate 178 is mounted upstream of the needle discharge, whereby the filtered air forms a sheath surrounding the needle. If desired, the air can be preheated, and also humidified with water vapor or a vapor of the liquid medium. A relatively large orifice 180 is formed in a downstream end wall 182 of the nebulizer.

A graphite plate 184 is mounted on a metal support rod 186, and positioned immediately downstream of the exit orifice. The plate and support rod are grounded, whereby sample solution droplets are attracted to the plate, as well as being carried toward the plate by the air sheath. A motor 188 rotates plate 184 through rod 186, about an axis through the center of the rod, which tends to even the distribution of collected droplets over the surface of the plate.

The different structure of nebulizer 164 is suited to its purpose. In particular, droplets intentionally are not evaporated to completely dry the aerosol. Rather, sufficient medium is retained, at least initially, to surround and support the molecule under study.

Following deposition, plate 184 is removed from rod 186. Individual molecules are analyzed, e.g. using atomic force microscopy, scanning tunneling microscopy, or transmission electron microscopy.

A feature of the present invention is that the electrospray nebulizer provides a heretofore unachieved degree of control over the nebulizer output, in terms of aerosol size as well as uniformity. Factors such as conductivity of the liquid solution sample, flow rate at which the sample is supplied to the nebulizer, and the voltage applied to form the electrical field, control the diameter of primary droplets. More particularly, droplet size can be reduced by increasing solution conductivity, increasing the needle/plate voltage, and reducing the liquid flow rate. The following table of experimental results illustrates the effect of changes in flow rate and conductivity on droplet size:

| FLOW RATE MICROLITERS PER MINUTE | SPECIFIC CONDUCTIVITY MICROMHOS PER CM | DROPLET SIZE MICROMETERS |
|---|---|---|
| 0.76 | 830 | 0.86 |
| 0.5 | 813 | 0.8 |
| 0.2 | 1,190 | 0.53 |
| 0.075 | 2,600 | 0.256 |

In practice, the conductivity required for a given droplet size and flow rate can vary widely depending on the solvents involved, e.g. over a range of from about 10-100,000 micromhos per centimeter.

Given the uniform distribution of residue throughout a liquid sample, the size of dried residue particles exhibits similar uniformity and is subject to the same control. Consequently, a nebulizer of the type disclosed can be used as a source of uniformly sized particles, over different ranges and levels of sizes, to test a filter, and to characterize a particle analyzing instrument such as a condensation particle counter.

Thus in accordance with the present invention, an electrospray nebulizer is provided for producing primary droplets of uniform size and substantially below one micron in diameter. Primary droplets are subjected to neutralizing radiation shortly after their formation, to prevent Rayleigh disintegration and thereby maintain a high degree of size uniformity despite reduction in droplet size due to solvent evaporation. The nebulizer thus produces an aerosol of smaller, more uniformly sized particles. The performance of particle analyzing instruments receiving the nebulizer output is substantially enhanced, and the nebulizer can provide a source of uniformly size particles for testing of such instruments.

What is claimed is:
1. An apparatus for generating aerosols, including:
an electrospray means having an electrospray inlet and a discharge, for receiving a liquid sample at the electrospray inlet and electrostatically generating multiple substantially uniformly sized electrically charged droplets of the liquid sample at the discharge; a means for supplying the liquid sample to the electrospray means; and an evaporation means defining a droplet evaporation region proximate the electrospray discharge and extending downstream thereof, for reducing the size of the droplets by evaporation as the droplets progress downstream through the evaporation region, to form an aerosol of the sample; and a charge neutralizing means disposed proximate the discharge and along the evaporation region, for reducing the electrical charge of each droplet of the liquid sample as the droplet exits the electrospray means, and for continuing to reduce the electrical charge of each droplet as it progresses through the evaporation region, to prevent the droplets from disintegrating due to repulsive Coulombic forces, whereby said aerosol is substantially monodisperse.

2. The apparatus of claim 1 wherein:
the liquid sample comprises an electrically conductive liquid and a substantially non-volatile material uniformly dispersed throughout the liquid, and wherein the aerosol includes particles of a substantially non-volatile residue consisting essentially of the material.

3. The apparatus of claim 2 further including:
a means for retarding the rate of evaporation of the liquid.

4. The apparatus of claim 3 wherein:
said means for retarding the rate of evaporation include means for introducing vapor of the liquid into the evaporation region.

5. The apparatus of claim 2 further including:
an aerosol collection means proximate to and downstream of the evaporation region.

6. The apparatus of claim 5 wherein:
said aerosol collection means comprises a graphite plate.

7. The apparatus of claim 2 further including:
a means for retarding the rate of evaporation of the liquid.

8. The apparatus of claim 7 wherein:
said means for retarding the rate of evaporation include means for introducing vapor of the liquid into the evaporation region.

9. The apparatus of claim 2 wherein:
the liquid has a predetermined specific conductivity within the range of from about 10 micromhos/cm to about 100,000 micromhos/cm.

10. The apparatus of claim 9 wherein:
the electrically conductive liquid includes water, and a volatile, ionizable solute.

11. The apparatus of claim 2 further including:
a particle counting means disposed downstream of the evaporation region to receive the aerosol.

12. The apparatus of claim 11 wherein:
the particle counting means is a condensation particle counter.

13. The apparatus of claim 2 further including:
an aerosol collection means proximate to and downstream of the evaporation region.

14. The apparatus of claim 13 wherein:
said aerosol collection means comprises an electrically charged plate.

15. The apparatus of claim 2 further including:
a particle separation means disposed downstream of the evaporation region to receive the aerosol, for separating particles of the aerosol based upon the electrical mobility of the individual particles.

16. The apparatus of claim 15 wherein:
the separation means comprises an electrostatic classifier.

17. The apparatus of claim 2 further including:
a particle analyzing means disposed downstream of the evaporation region to receive the aerosol.

18. The apparatus of claim 17 wherein:
the particle analyzing means includes an electrostatic classifier receiving the aerosol, and a condensation particle counter downstream of the electrostatic classifier.

19. The apparatus of claim 17 wherein:
the particle analyzing means includes means providing a surface for collecting the aerosol for analysis by microscopy.

20. The apparatus of claim 2 wherein:
the liquid is a solvent, and the material is a solute dissolved in the liquid.

21. The apparatus of claim 1 wherein:
the evaporation means includes an enclosure defining an evaporation chamber having an entrance orifice and an exit, and providing said evaporation region.

22. The apparatus of claim 21 wherein:
the enclosure further defines an electrospray chamber adjacent the evaporation chamber, said discharge being within the electrospray chamber; and wherein the enclosure further includes an electrically conductive wall separating the evaporation chamber from the electrospray chamber and electrically biased to attract the electrically charged droplets toward the evaporation chamber, and the entrance orifice is disposed in the electrically conductive wall.

23. The apparatus of claim 22 wherein:
the neutralizing means includes a first ion producing means in the evaporation chamber near the entrance orifice.

24. The apparatus of claim 23 wherein:
the neutralizing means further includes a second ion producing means, located in the electrospray chamber.

25. The apparatus of claim 23 wherein:
the ion producing means comprises at least one of the following: a radioactive material emitting alpha particles, a radioactive material emitting beta particles, a corona discharge source, and a photon ionization source.

26. The apparatus of claim 22 further including:
a means for supplying a gas to the electrospray chamber and flowing in a stream from the electrospray chamber into the evaporation chamber, thereby tending to carry the electrically charged droplets into the evaporation chamber.

27. The apparatus of claim 26 further including:
a means in the electrospray chamber for substantially reducing the turbulence of the gas stream.

28. The apparatus of claim 1 further including:
a means for providing a gas stream along the electrospray means, for carrying the electrically charged droplets downstream through the evaporation region.

29. The apparatus of claim 1 wherein:
the electrospray means includes an elongate capillary needle defining an elongate lumen having an inlet port and an exit port on opposite ends of the capillary needle, said exit port providing said discharge.

30. An apparatus for analyzing submicron droplets and particles, including:
an electrospray means having an electrospray inlet and a discharge, for receiving a liquid sample at the electrospray inlet and electrostatically generating multiple substantially uniformly sized electrically charged droplets of the liquid sample at the discharge; a means for supplying the liquid sample to the electrospray means at a controlled rate; and an evaporation means defining a droplet evaporation region proximate the electrospray discharge and extending downstream thereof, for reducing the size of the droplets by evaporation as the droplets progress downstream through the evaporation region, to form an aerosol of the liquid sample;

a charge neutralizing means for reducing the charge of each droplet as the droplet progresses through the evaporation region by an amount sufficient to prevent droplet fragmentation due to Coulombic forces, whereby said aerosol is substantially monodisperse;

a particle separation means disposed downstream of the evaporation region, for receiving the aerosol from the electrospray means and for separating particles of the aerosol based on the electrical mobility of the particles; and a particle counting means disposed downstream of the particle separation means, for counting the particles received from the separation means.

31. The apparatus of claim 30 wherein:
said particle separation means comprises an electrostatic classifier.

32. The apparatus of claim 30 wherein:
said particle counting means comprises a condensation particle counter.

33. The apparatus of claim 30 further including:
a means for providing a gas stream along the electrospray means, for carrying the electrically charged droplets downstream through the evaporation region.

34. A process for forming multiple submicron droplets generally uniform in size, including the steps of:
providing a liquid sample at a steady supply rate to an electrospray device, and generating multiple, substantially uniformly sized, electrically charged droplets of the liquid sample at a discharge of the electrospray device;

transporting the electrically charged droplets downstream of the discharge through an evaporation region, to controllably reduce the size of the droplets by evaporation as the droplets progress through the evaporation region;

while so transporting the droplets, reducing the electrical charge of each droplet as it emerges from the discharge; and thereafter continually reducing the electrical charge of each droplet as it is so transported to prevent the droplet from disintegrating due to repulsive Coulombic forces.

35. The process of claim 34 wherein:
the liquid sample includes an electrically conductive liquid and a substantially non-volatile material dispersed substantially uniformly throughout the liquid, whereby the electrically charged droplets include the liquid and a non-volatile residue consisting essentially of the material.

36. The process of claim 35 wherein:
the step of controllably reducing the size of the droplets includes evaporating substantially all of the electrically conductive liquid to form particles of the non-volatile residue.

37. The process of claim 35 further including the step of:
retarding the rate of evaporation of the electrically conductive liquid as the droplets progress through the evaporation region.

38. The process of claim 37 wherein:
the electrically conductive liquid is a solvent, and the step of retarding the rate of evaporation includes supplying a gas stream to the evaporation region, with the gas stream including a vapor of the solvent.

39. The process of claim 35 further including the step of:
retarding the rate of evaporation of the electrically conductive liquid as the droplets progress through the evaporation region.

40. The process of claim 39 wherein:
the electrically conductive liquid is a solvent, and the step of retarding the rate of evaporation includes supplying a gas stream to the evaporation region, with the gas stream including a vapor of the solvent.

41. The process of claim 34 including the further step of:
controlling the specific conductivity of the liquid sample, whereby the conductivity is within the range of from about 10 micromhos/cm to about 100,000 micromhos/cm.

* * * * *